US00PP10696P

United States Patent [19]

McGredy

[11] Patent Number: Plant 10,696

[45] Date of Patent: Nov. 24, 1998

[54] HYBRID TEA ROSE PLANT NAMED 'MACRENO'

[75] Inventor: Sam McGredy, Auckland, New Zealand

[73] Assignee: DeVor Nurseries, Inc., Watsonville, Calif.

[21] Appl. No.: 742,141

[22] Filed: Oct. 31, 1996

[51] Int. Cl.[6] ..... A01H 5/00

[52] U.S. Cl. ..... Plt./11

[58] Field of Search ..... Plt./11, 17, 12, Plt./16

[56] References Cited

PUBLICATIONS

UPOUROM, Plant Uariety Database, 1997/03, GTI Jouve Retrieval Software, listing for 'Macreno'.

*Primary Examiner*—Howard J. Locker
*Attorney, Agent, or Firm*—Christie, Parker & Hale, LLP

[57] ABSTRACT

A hybrid tea rose plant variety producing salmon bi-color flowers.

1 Drawing Sheet

BACKGROUND OF THE INVENTION

The present invention relates to a new and distinct hybrid tea rose variety which was originated by my crossing as seed parent the variety known as 'Waiheke' and as pollen parent the variety known as 'Las Vegas'. The varietal denomination of this new rose is 'Macreno.'

SUMMARY OF THE INVENTION

Among the novel characteristics possessed by this new variety which distinguish it from its parents and other varieties of which I am aware are its attractive salmon bi-color flowers borne on long, strong stems.

Asexual reproduction by budding of the new variety as performed in Watsonville, Calif., shows that the foregoing and other distinguishing characteristics come true to form and are established and transmitted through succeeding propagations. Other known forms of asexual reproduction for roses may be also employed.

Comparison With Parents

'Macreno', is a smallish flowered salmon and yellow bi-color hybrid tea. 'Walheke' is a straight medium pink colored grandiflora. 'Las Vegas' is a much bigger, longer flower than 'Macreno', the plant is more upright. While it is a bi-color, the general coloring is much more orange-scarlet as compared to 'Macreno'.

BRIEF DESCRIPTION OF ILLUSTRATIONS

The accompanying illustration shows typical specimens of the vegetative growth and flowers of the new variety in different stages of development and depicted in color as nearly true as it is reasonably possible to make the same in a color illustration of this character.

DESRIPTION OF THE NEW VARIETY

Parentage: Seedling.
*Seed parent:* 'Waiheke'.
*Pollen parent:* 'Las Vegas'.
Class: Hybrid Tea.

The following is a detailed description of the new variety, from specimens grown outdoor glass in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

Flower

Blooming Habit: Continuous.

A. Bud:
- (1) *Size.*—Medium about 4 cm to 5 cm long, about 2.5 cm to 3 cm wide.
- (2) *Form.*—Pointed.
- (3) *Color.*—When sepals first divide, bud color is near 48C.
- (4) *Sepals.*—About 3 to 3.5 cm long, sepals divide and reflex as bloom opens; some sepals are foliaceous with leaf shaped ends. Color: Near 144A at base and tip, near 166A at center; undersurface near 144A in center and near 144C at tip.
- (5) *Peduncle.*—Length: About 8 cm. Aspect: Rough, many small prickles. Strength: Erect. Color: Near 152B with near 183A shading.
- (6) *Bracts.*—About 2 to 3.

B. Bloom:
- (1) *Size.*—Average size when fully expanded — about 11 cm.
- (2) *Borne.*—Singly.
- (3) *Form.*—Imbricated, petals reflex at maturity.
- (4) *Petalage.*—Number of petals under normal conditions — about 40 to 44.
- (5) *Color* (⅓–½ *open*).—Outer petals — Red group 43D; Undersurface near 3C. Inner petals — Top surface: top near 41A; Undersurface: near 3D. Base of petals: Near 9B. General tonality from a distance: Dark salmon bi-color.
- (6) *Color* (*Fully open*).—Outer petals — Top surface: Outer edge — near 45D with rest of petal near 43C; Undersurface: outer edge — near 39D with rest of petal near 39C. Inner petals — Top surface: Outer edge — near 43B with rest of petal near 43C; Undersurface: Outer edge — near 37B with rest of petal near 1C. Base of petals: Center of base: Near 3B with rest of base near 2C. General tonality from a distance: Dark salmon-orange.
- (7) *Color change.*—Top surface lightens and undersurface fades. Petal top surface: Near 43C. Petal undersurface: Near 4D. Base of petals: Near 3B. General tonality at a distance: Salmon-orange.

C. Petals:
(1) *Texture.*—Thick, smooth.
(2) *Appearance.*—Inside: semi-velvety, semi-satiny.
(3) *Form.*—Elliptic.
(4) *Arrangement.*—Imbricated and ruffled.
(5) *Petaloids.*—Many, about 6 to 8.
(6) *Fragrance.*—Slightly fruity.
(7) *Lasting quality.*—On plant about 5 to 7 days; about 10 to 12 days as cut flower.
(8) *Persistence.*—Petals drop off cleanly.

Reproductive Organs

A. Stamens
(1) *Arrangement.*—Irregularly arranged around styles.
(2) *Anthers.*—Color — near 22A.
(3) *Filaments.*—Color — near 12A.
(4) *Pollen.*—Color —near 22A.

B. Pistils:
(1) *Styles.*—Bunched, even length.
(2) *Stigmas.*—Color — near 162B.

C. Characteristics of hips: Globular, about 1.8 cm wide by about 2.0 cm long, near 144A; seeds do not protrude.

Plant

A. Form: Upright.

B. Growth: Vigorous; about 106 cm to about 147 cm in height at first season.

C. Foliage: Compound 3 to 5 leaflets.
(1) *Size.*—Medium, about 12 cm to 13 cm; largest leaflet about 3 cm to 5.8 cm long; oval, denticulate edging.
(2) *Quantity.*—*Abundant.*
(3) *Color.*—New foliage — upper side near 187A, underside near 183B; mature foliage — upper side near 146A, underside near 146B.
(4) *Shape.*—Oval.
(5) *Texture.*—Upper side leathery, glossy; underside leathery, matte.
(6) *Edge.*—Serrate.
(7) *Serration.*—Denticulate.
(8) *Leaf stem.*—*Color — medium green.*
(9) *Stipules.*—Parallel, middle enlarged and slightly bearded.
(10) *Rachis.*—Smooth.
(11) *Petioles.*—Top near 146A, underside near 146C.
(12) *Auricle.*—Curving downwardly, thin.
(13) *Resistance to disease.*—Good resistance to blackspot, mildew and rust.

D. Wood:
(1) *New wood.*—Color near 183B, bark smooth.
(2) *Old wood.*—Color near 144A, bark smooth.

E. Flower stem: About 40 cm to about 81 cm from last cut.

F. Thorns:
(1) *Thorns.*—Quantity: On main stalk few; laterals from stalk, moderate. Form: Slightly wing-shaped, straight sides. Length: About 1 to 1.2 cm long. Color: Near 187B. Position: Regular.
(2) *Prickles.*—Many.

G. Winter hardiness: Winter hardy in Watsonville, Calif.

I claim:

1. A new and distinct variety of hybrid tea rose, substantially as shown and described.

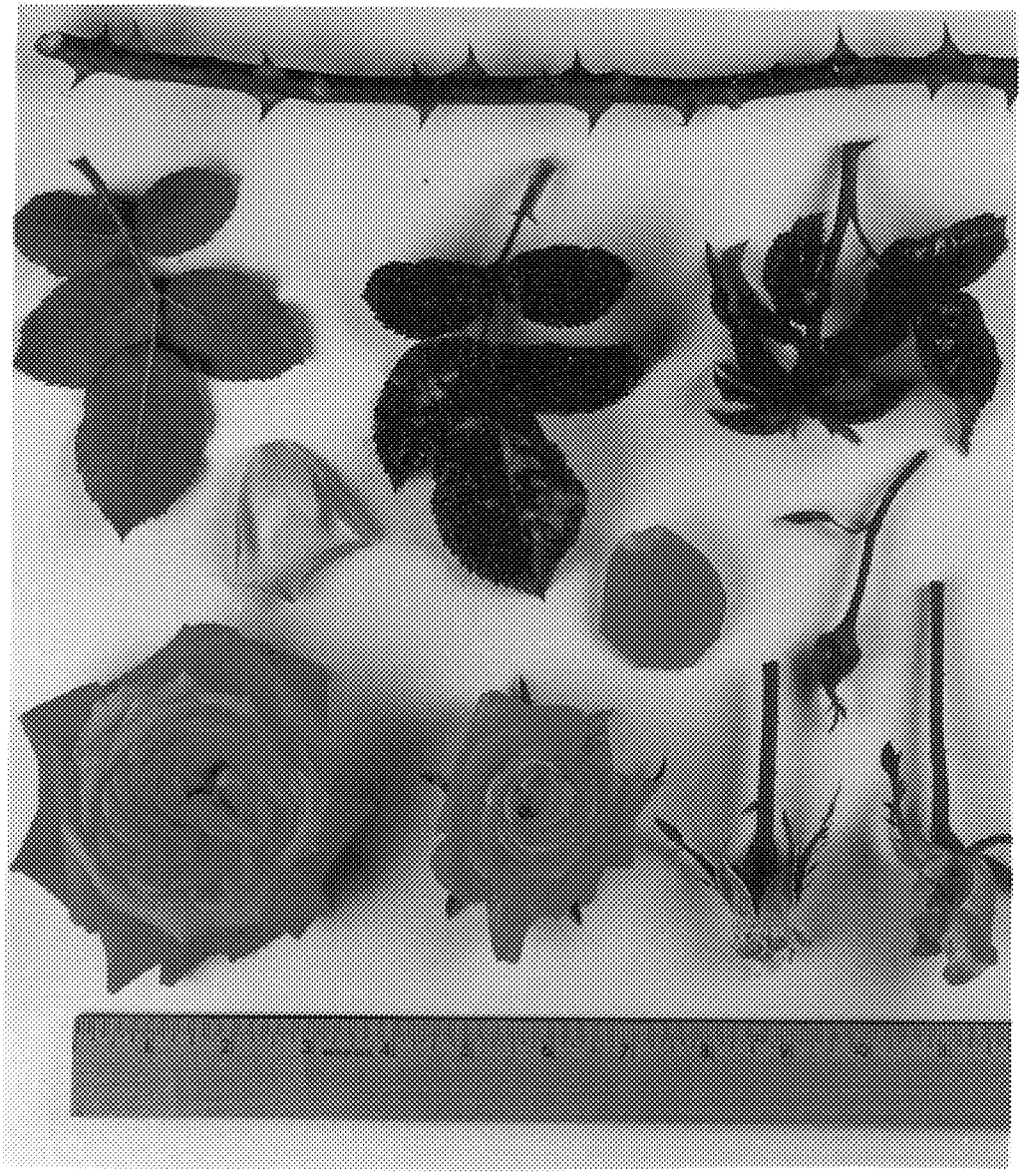

* * * * *